United States Patent [19]

Lozhenko et al.

[11] Patent Number: 4,986,628
[45] Date of Patent: Jan. 22, 1991

[54] LIGHT GUIDE DEVICE FOR PHOTOTHERAPY

[76] Inventors: Alexandr S. Lozhenko, Nadsonovsky tupik, 5, kv. 32, Moskovskaya oblast, Pushkino; Vladimir I. Rechitsky, Peschany pereulok, 8, kv. 18; Viktor N. Shendalev, ulitsa Vucheticha, 4, kv. 30, both of Moscow, all of U.S.S.R.

[21] Appl. No.: 477,821
[22] PCT Filed: Aug. 23, 1988
[86] PCT No.: PCT/SU88/00164
   § 371 Date: Apr. 18, 1990
   § 102(e) Date: Apr. 18, 1990
[87] PCT Pub. No.: WO90/02353
   PCT Pub. Date: Mar. 8, 1990

[51] Int. Cl.$^5$ .............................................. G02B 6/16
[52] U.S. Cl. .................................. 350/96.29; 350/96.10; 350/96.15; 350/96.20; 362/32
[58] Field of Search ............... 350/96.10, 96.15, 96.18, 350/96.20, 96.23, 96.24, 96.25, 96.26, 96.29, 96.30; 362/32; 128/4, 5, 6

[56] References Cited

U.S. PATENT DOCUMENTS

| | | | |
|---|---|---|---|
| 4,516,022 | 5/1985 | Lindgren | 250/227 |
| 4,639,078 | 1/1987 | Sheem | 350/96.21 |
| 4,740,047 | 4/1988 | Abe et al. | 350/96.15 |
| 4,801,187 | 1/1989 | Elbert et al. | 350/96.15 |
| 4,822,123 | 4/1989 | Mori | 350/96.10 |
| 4,895,420 | 1/1990 | Waymouth | 350/96.10 |

*Primary Examiner*—Frank Gonzalez
*Attorney, Agent, or Firm*—Burgess, Ryan & Wayne

[57] ABSTRACT

A light guide device for phototherapy has an optical fiber light guide (1) and a light scattering member at its distal end. A protective envelope (4) of the light guide (1) protrudes beyond an end face (6) of its distal end and defines with this end face (6) a closed space which is filled up entirely with an optically turbid medium (7) which defines the light scattering member (5).

1 Claim, 1 Drawing Sheet

LIGHT GUIDE DEVICE FOR PHOTOTHERAPY

TECHNICAL FIELD

The invention relates to light guide devices for the transmission of a radiation energy, and in particular, it deals with light guide devices for phototherapy.

BACKGROUND ART

Known in the art is a light guide device for phototherapy comprising an optical fiber light guide and a light cattering member in the form of a bare light guiding strand of the light guide the periphery of which is treated with hydrofluoric acid (Optics and Laser Technology. 1984, February. H. Fujii et al. "Light Scattering Properties of a Rough-Ended Optical Fiber", pp. 40, 41).

This device cannot be used for carrying out intracavitary laser treatment procedures because of high danger: the light scattering member is in the form of a brittle member which is very likely to be broken in the patient body.

Known in the art is a light guide device for phototherapy comprising an optical fiber light guide having a light guiding strand, light reflecting and protective envelopes and a light scattering member provided at the distal end of the optical fiber light guide (Laser in Surgery and Medicine, No. 6, 1986. M. Arnfield et al. "Cylindrical Irradiator Fiber Tip for Photodynamic Therapy. p. 151).

In this light guide device for phototherapy, the light scattering member is in the form of a sleeve having end faces of its walls cemented to a bare portion of a light guiding strand of the optical fiber light guide, a layer of epoxy resin being applied to the inner surface of the sleeve walls.

This device cannot ensure safety of a patient in carrying out intracavitary laser treatment procedures, i.e. it is dangerous and may cause injury.

This device is also complicated in the manufacture. Moreover, this device can only ensure one type of the indicatrix of light distribution of the radiation, i.e. it cannot ensure matching of the shape of indicatrix of light distribution of the radiation to the shape of a pathological focus so as to optimize the effect of the therapy factor.

DISCLOSURE OF THE INVENTION

The invention is based on the problem of providing a light guide device for phototherapy in which a protective envelope of an optical fiber light guide in combination with a light scattering member are made in such a manner at to ensure absolute guarantee against injury of a patient and to optimize the effect of the therapy factor by matching the shape of indicatrix of light distribution of the radiation to the shape of a pathological focus while ensuring a simple design of the light guide device.

This is accomplished by that in a light guide device for phototherapy comprising an optical fiber light guide having a light guiding strand a light reflecting envelope and a protective envelope, and a light scattering member provided at a digital end of the optical fiber light guide, according to the invention, the protective envelope of the optical fiber light protrudes beyond the end face of the dictal end of the optical fiber light guide and defines a closed space therewith, and the light scattering member is made of an optically turbid medium which is in contact with the end face of the optical fiber light guide and which fills up the entire closed space.

This structural embodiment of the light guide device for phototherapy makes it possible to completely avoid injuries of a patient in carrying out intracavitary laser treatment procedures, i.e. it makes it possible to achieve high reliability in operation and to optimize the effect of the therapy factor with a simple design of the device.

BRIEF DESCRIPTION OF THE DRAWINGS

The invention will now be described with reference to specific embodiments illustrated in the accompanying drawings, in which.

BEST MODE FOR CARRYING OUT THE INVENTION

Figure 1:
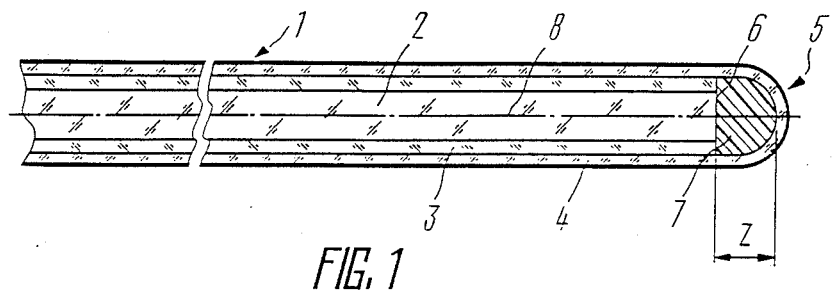
FIG. 1 is a longitudinal section view of a light guide device for phototherapy according to the invention.

A light guide device for phototherapy according to the invention comprises an optical fiber light guide 1 (FIG. 1) having a light guiding strand 2, a light reflecting envelope 3 and a protective envelope 4, and a light scattering member 5 provided at a distal end of the optical fiber light guide 1.

The protective envelope 4 protrudes beyond an end face 6 of the distal end of the optical fiber light guide 1 and defines a closed space with the end face 6. The light scattering member 5 is made of an optically turbid medium 7 which is in contact with the end face 6 of the optical fiber light guide 1 and which fills up the entire closed space.

The optically turbid medijm may be in the form of a cement based on epoxy, low-molecular or polyamide resins.

The light guide device for phototherapy according to the invention functions in the following manner.

A laser radiation (not shown) propagates along the light guiding strand 2 (FIG. 1) of the optical fiber light guide 1 and enters the light scattering member 5 in which it is scattered in the optically turbid medium 7. The scattered radiation passes through the protective envelope 4 and through the distal end of the light guide 1 of the device according to the invention.

Depending on the radiation attenuation coefficient in the optically turbid medium 7 and length of the light scattering member 5 along the optical path 8 of the light guide 1, various configuration of indicatrixes of light distribution of the radiation may be obtained.

Thus, length z of the light scattering member 5 along the optical path 8 of the light guide 1 depending on the attenuation coefficient $\epsilon$ of the optically turbid medium 7 of this member 5 can ensure various configurations of indicatrixes of the radiation with uniformity of radiation which is efficient enough for carrying out laser treatment procedures.

Figure 2:
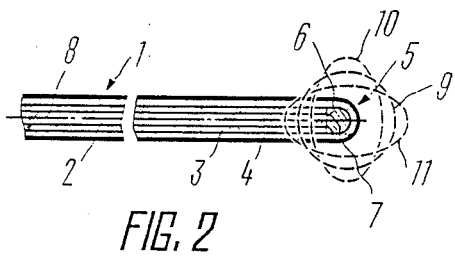
FIG. 2 shows indicatrixes of light distribution of the radiation in the form of ellipsoids and a sphere obtained with the aid of a light guide device of FIG. 1.

With $$z < \frac{1}{\epsilon} \text{ or } z < \frac{1}{\epsilon},$$

indicatrixes 9, 10 and 11 (FIG. 2) of light distribution of the radiation are in the form of a sphere or ellipsoids, respectively. These indicatrixes are widely used for phototherapy of pulmonary abscess, pyothorax, maxillary sinusitis, chronic gastroduodenal ulcers.

Figure 3:
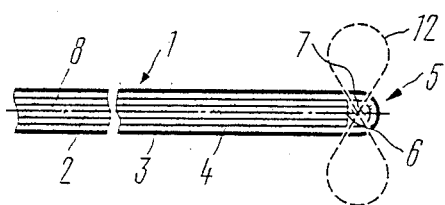
FIG. 3 is indicatrix of light distribution in the form of a torus obtained with the aid of the light guide device of FIG. 1.

With $$z = \frac{1}{\epsilon},$$

the indicatrix 12 (FIG. 3) of light distribution of the radiation is in the form of a torus, This configuration of the indicatrix is used for phototherapy of tubular cavities with localization of pathological foci on the walls, e.g. chemical burns of the esophagus, uretritis, non specific uretritis.

The possibility of ensuring a pre-set type of indicatrixes of light distribution of the radiation allows an optimum exposure to be obtained, and the therapy factor of such exposure can be used to the maximum possible extent.

Therefore, the device according to the invention may be used for acting with laser radiation directly upon pathological foci localized in hardly accessible tubular cavities of a patient body which are of a small size (1.2–1.8 mm), e.g. wound surfaces and postoperation sutures of the ureter, inflammation of the auditory tube, pyothorax and pulmonary abscess.

In addition, the light guide device according to the invention for phototherapy features high reliability in use and simple structure.

INDUSTRIAL APPLICABILITY

The invention may be successfully used in the medicine for phototherapy in carrying out intracavitary laser treatment procedures with localization of pathological foci in hardly accessible cavities of a patient body.

We claim:

1. A light guide device for phototherapy, comprising an optical fiber light guide having a light guiding strand, a light reflecting envelope and a protective envelope, and a light scattering member provided at a distal end of the optical fiber light guide, characterized in that the protective envelope (4) of the optical fiber light guide (1) protrudes beyond an end face (6) of the distal end of the optical fiber light guide (1) and defines a closed space with the end face (6), and in that the light scattering member (5) is made of an optically turbed medium (7) which is contact with the end face (6) of the optical fiber light guide (1) and which fills up the entire closed space.

* * * * *